United States Patent
Jayaraman et al.

(10) Patent No.: US 6,315,009 B1
(45) Date of Patent: Nov. 13, 2001

(54) FULL-FASHIONED GARMENT WITH SLEEVES HAVING INTELLIGENCE CAPABILITY

(75) Inventors: Sundaresan Jayaraman, Atlanta; Sungmee Park, Tucker, both of GA (US)

(73) Assignee: Georgia Tech Research Corp., Atlanta, GA (US)

( * ) Notice: Subject to any disclaimer, the term of this patent is extended or adjusted under 35 U.S.C. 154(b) by 0 days.

(21) Appl. No.: 09/713,147

(22) Filed: Nov. 14, 2000

Related U.S. Application Data

(63) Continuation-in-part of application No. 09/157,607, filed on Sep. 21, 1998, now Pat. No. 6,145,551, and a continuation-in-part of application No. 09/273,175, filed on Mar. 19, 1999.
(60) Provisional application No. 60/085,266, filed on May 13, 1998.

(51) Int. Cl.[7] .................................................. D03D 3/02
(52) U.S. Cl. ..................................... 139/387 R; 139/55.1; 2/455; 2/905
(58) Field of Search ................................ 139/387 R, 55.1, 139/388, 387; 2/455, 905, 102, 243; 128/664, 639; 428/68, 196, 257, 195, 36

(56) References Cited

U.S. PATENT DOCUMENTS

| | | |
|---|---|---|
| 2,579,383 | 12/1951 | Goudsmit . |
| 2,935,096 | 5/1960 | Cole . |
| 3,020,935 | 2/1962 | Balis . |
| 3,409,007 | 11/1968 | Fuller . |
| 4,299,878 | 11/1981 | Rheaume . |
| 4,572,197 | 2/1986 | Moore et al. . |
| 4,580,572 | 4/1986 | Granek et al. . |
| 4,606,968 | 8/1986 | Thornton et al. . |
| 4,668,545 | 5/1987 | Lowe . |
| 4,727,603 | 3/1988 | Howard . |
| 5,103,504 | 4/1992 | Dordevic . |
| 5,212,379 | 5/1993 | Nafarrate et al. . |
| 5,316,830 | 5/1994 | Adams, Jr. et al. . |
| 5,415,204 | 5/1995 | Kitamura . |
| 5,436,444 | 7/1995 | Rawson . |
| 5,592,977 | 1/1997 | Kikuchi et al. . |
| 5,624,736 | 4/1997 | DeAngelis et al. . |
| 5,636,378 | 6/1997 | Griffith . |
| 5,694,645 | 12/1997 | Triplette . |

*Primary Examiner*—John J. Calvert
*Assistant Examiner*—Robert H. Muromoto
(74) *Attorney, Agent, or Firm*—Todd Deveau; Ryan A. Schneider; Troutman Sanders LLP

(57) ABSTRACT

The invention comprises a full-fashioned weaving process for the production of a woven garment which can accommodate and include sleeves. The garment is made of only one, single integrated fabric and has no discontinuities or seams. Additionally, the garment can include intelligence capability, such as the ability to monitor one or more body vital signs, or garment penetration, or both, by including a selected sensing component or components in the weave of the garment.

20 Claims, 5 Drawing Sheets

. Full Fashion Garment With Integrated Sleeves

Drawing-In-Draft

Figure 1. Full Fashion Garment With Integrated Sleeves

Fig 2. Drawing-In-Draft

Figure 3. Lifting Plan

FULL-FASHIONED GARMENT WITH SLEEVES HAVING INTELLIGENCE CAPABILITY

This application is a continuation-in-part of U.S. Ser. No. 09/157,607, filed on Sep. 21, 1998, now U.S. Pat. No. 6,145,551, and is a continuation-in-part of U.S. Ser. No. 09/273,175, filed on Mar. 19, 1999 and claims benefit of provisional application Ser. No. 60/085,266, filed May 13, 1998.

BACKGROUND OF THE INVENTION

1. Field of the Invention

The present invention relates to a full-fashioned weaving process for the production of a single-piece woven garment which can accommodate and include sleeves. The garment is made of only one single integrated fabric which has no discontinuities or seams. Additionally, the garment can include an integrated infrastructure for collecting, processing, transmitting and receiving information, giving it intelligence capability.

2. Background of the Art

In weaving, two sets of yarns known as warp and filling yarns, respectively, are interlaced at right angles to one another on a weaving machine or loom. Traditional weaving technologies typically produce a two-dimensional fabric. To fashion a three-dimensional garment from such a woven fabric traditionally requires cutting and sewing of the fabric.

Tubular weaving is a special variation of traditional weaving in which a fabric tube is produced on the loom. However, tubular weaving, until now, has not been available to produce a full-fashioned woven garment, such as a shirt, because it was unable to accommodate discontinuities in the garment, such as armholes or sleeves, without requiring cutting and sewing.

Co-pending application U.S. Ser. No. 09/157,607 filed Sep. 21, 1998, now U.S. Pat. No. 6,145,551 to Jayaraman, et al., discloses a full-fashioned weaving process for the production of a woven garment having armholes. The garment is a single integrated piece in which there are no discontinuities or seams, and the armholes result from the weaving process itself, not from cutting or sewing. The process of the Jayaraman patent, however, does not provide for the weaving of a full-fashioned garment having sleeves.

A need therefore exists for a process to produce a full-fashioned woven garment with sleeves which eliminates the need for cutting and sewing fabric parts to fashion the garment. It is such a process and product to which the present invention is primarily directed. When the full-fashioned weaving process of the present invention is employed, the additional step of sewing side seams and sleeves required for a two-dimensional fabric is avoided.

Alternatively, co-pending application U.S. Ser. No. 09/273,175, filed on Mar. 19, 1999 by Jayaraman et al., discloses a fabric or garment which includes an integrated infrastructure for collecting, processing, transmitting and receiving information. The garment functions as a "wearable motherboard," which, by utilizing the interconnection of electrical conductive fibers, integrates many data-collecting sensors into the garment without the need for multiple stand-alone wires or cables. The information may be transmitted to several monitoring devices through a single electronic lead or transceiver.

Utilizing the weaving technique of the present invention and the interconnection of electrical conductive fibers or optical fibers or both of the co-pending Jayaraman applications, it is possible to produce a full-fashioned woven garment with sleeves which incorporates an integrated infrastructure for collecting, processing, transmitting and receiving information.

SUMMARY OF THE INVENTION

It is, therefore, an object of the present invention to provide a weaving process to produce a full-fashioned woven garment with sleeves, which garment is comprised of only a single integrated piece and has no discontinuities or seams.

It is a further object of the invention to fashion a garment which can accommodate sleeves, for example, a shirt, without requiring cutting and sewing of the fabric, except for the rounding or finishing of the neck, if such is desired.

It is yet a further object of the present invention to provide a full-fashioned garment with sleeves which garment can include intelligence capability, such as the ability to monitor one or more body physical signs and/or penetration of the garment, and a process for making such a garment.

In the full-fashioned woven garment of the present invention, three different weave structures are used: one is a tubular structure section; the second is a double layer structure section and the third is a self-stitched layer structure section. Unlike the structure of a regular shirt made of woven fabric where the front, back and sleeves need to be sewn together to make a "one-piece" garment, the fabric of the present invention emerges as an integrated "one-piece" garment with sleeves during the weaving process. In the tubular section of the woven fabric, only one thread or set of threads is interlaced helically and continuously on the front and back. This process is described in U.S. Ser. No. 09/157,607, which is incorporated by reference in its entirety as if fully set forth herein.

The warp threads are grouped into two sets, one for the body of the garment and the other for the two sleeves. In the drawing-in-draft for the tubular structure section of the body of the woven fabric of the present invention, two different sets of warp threads are used alternately—one is for the front and the other is for the back of the fabric. A lifting plan provides the sequence of harness movements. The harnesses of the loom are lifted by the lifting plan representing the front and back of the fabric alternately. Since this is a double cloth structure, both the front and back warp threads are placed in the same dent of the reed of the loom.

Although the filling for a tubular fabric needs only one set of continuous threads, the full-fashioned woven garment of the present invention, when accommodating sleeves, requires two sets of threads. This is because of the innovative nature of the double layer structure section of the garment. In the self-stitched structure section, the front and back sets of warp threads are woven together with the two sets of filling threads creating the closures for the sleeves.

One innovative facet of our full-fashioned woven garment lies in the creation of a sleeve by way of the self-stitched layer structure section in combination with the double layer structure section. Unlike the tubular structure section, in the double layer structure section of the garment, there are two sets of threads, and a double-layer structure is used separately for the front and back of the garment. Since two sets of threads are used from the tubular structure section, the fabric of the self-stitched layer section in combination with the double layer structure section can be woven continuously from the tubular structure section. Then a stand-alone double layer structure section can be woven from this combination self-stitched—double layer structure section. The stand-alone double layer structure section can then be followed continuously by another combination self-stitched—double layer structure section. Likewise, the tubular structure section can be woven continuously from this combination self-stitched—double layer structure section. In this manner, for example, a full-fashioned woven garment may be made by continuously weaving a first tubular structure section as described, followed by a combination self-stitched—double layer structure section, then a stand-alone double layer structure section followed by a combination self-stitched—double layer structure section and then a second tubular structure section from the combination self-stitched—double layer structure section. Other combinations of continuously woven tubular structure, self-stitched structure section and double layer structure sections may also be made. Further, the full-fashioned weaving process of the present invention is not limited to the manufacture of a garment having sleeves, but is generally applicable to the manufacture of any full-fashioned garment which may require similar appendages.

In one particular embodiment, to accomplish such a woven garment, for example, an 8 harness loom, can be used. The loom's 8 harnesses are divided into two sets. Each set contains four harnesses. Among the four harnesses in each set, two harnesses are used for the front layer and the other two are used for the back layer of the garment. Since the lifting sequence for both sides of the garment is the same, the sleeves will be created simultaneously on both sides of the double layer structure section. In this manner, a single continuous woven garment is thereby produced in which sleeves are created.

In a further embodiment, the woven garment made in accordance with the present invention may be fashioned into a garment having intelligence capacity. The garment can be provided with means for monitoring one or more body vital signs, such as blood pressure, heart rate, and temperature, as well as for monitoring garment penetration. The one-piece sleeved structure allows for monitoring of vital signs under a patient's arm. Because of its seamless design, the sleeved garment is particularly useful for bed-ridden patients who have little mobility.

The woven garment consists of a base fabric ("comfort component"), and at least one sensing component. The sensing component can be either a penetration sensing material component, or an electrically conductive material component, or both. The preferred penetration sensing component is plastic optical fiber (POF). The preferred electrical conductive component is either a doped inorganic fiber with polyethylene, nylon or other insulating sheath, or a thin gauge metal wire with polyethylene sheath. Optionally, the fabric can include a form-fitting component, such as SPANDEX fiber, or a static dissipating component, such as NEGA-STAT, depending upon need and application. Each of these components can be incorporated into the full-fashioned weaving process of the present invention and thereby incorporated into a full-fashioned garment.

The sensing component can, among others, serve the following two main functions: (i) it can help detect projectile penetration; and (ii) it can serve as a "data bus" or "motherboard" for transferring information or data to and from other devices that are in communication with it. These capabilities can be used together or individually. The electrically conducting fibers can help carry information from sensors (mounted on the human/animal body or incorporated into the fabric structure) to monitoring devices to monitor heart rate, breathing rate, voice and/or any other desired body physical property. Thus, the present invention will create a flexible, sleeved garment, having a wearable information infrastructure that will facilitate the "plugging" in of devices for gathering/processing information concerning its wearer, utilizing the interconnection of electrical conductive fibers described in co-pending U.S. Ser. No. 09/273,175, incorporated herein by reference in its entirety as if fully set forth herein. Instead of both POF and conducting fibers, the fabric or garment can incorporate just conducting fibers and not the POF, or vice versa, depending on the desired end-use application. The number, length and pitch (thread spacing) of the POF can be varied to suit the desired end-use requirement. Similarly, the number, length and pitch (thread spacing) of the conducting fibers can be varied to suit the lend-use requirement.

The interconnection technology described below can be used to attach connectors to the fabric. Sensors can be incorporated into the fabric and/or mounted on the human being or animal and plugged into connectors incorporated into the fabric. The sensors can be used to monitor one or more body physical signs, such as vital signs. Thus, the fabric or garment of the present invention acts as a useful and flexible information infrastructure for information processing. By suitably tapping into the appropriate conducting fibers, the desired monitoring capabilities will be created. Alternately, the POF or other sensing component can serve as the "data bus" in place of or in addition to the conductive fibers for various applications.

It can be seen from the description herein of our invention that a full-fashioned weaving process is provided, by which a full-fashioned woven garment with sleeves can be made, which accommodates discontinuities in the garment, such as sleeves, without requiring cutting and sewing, and by which a garment with intelligence capability can be made. These and other objects and advantages of the present invention will become apparent upon reading the following specification and claims in conjunction with the accompanying drawing figures.

DETAILED DESCRIPTION OF THE ILLUSTRATIVE EMBODIMENT

Figure 1:
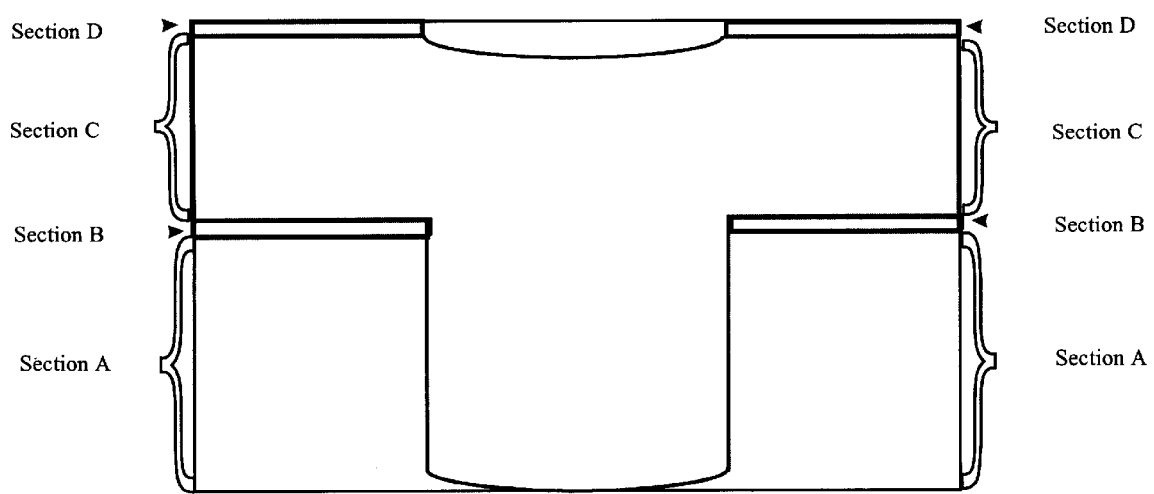
FIG. 1 illustrates the construction of a full-fashioned garment with integrated sleeves. (provided w/invention disclosure)

Referring now to the above figures, wherein like reference numerals represent like parts throughout the several views, the full-fashioned weaving process and product of the present invention will be described in detail.

A. The Full-Fashioned Weaving Process and Garment of the Present Invention

As illustrated in FIG. 1, a full-fashioned woven garment is made in accordance with the present invention. Three different weave structures are used: one is the tubular structure for the body of the garment; the second is the double layer structure and third is the self-stitched layer structure. The "self-stitched" layer structure in combination with the double layer structure referred to herein as the "combination self-stitched—double layer structure is used to form the sleeves without any seams in the garment. The ability to create a garment without seams results in a more comfortable, versatile garment.

To assist in the description of the present invention, reference will now be made to a garment, such as a sleeved shirt having a rounded neck similar to a knitted T-shirt, fashioned by the fully-fashioned weaving process of the present invention. However, it should be recognized that the present invention is not limited to only such a garment.

1. Description of Body Section of the Garment

Unlike the structure of a regular shirt made of woven fabric where the front, back and sleeves need to be sewn together to make a "one-piece" garment, the structure of the present invention emerges as an integrated "one piece" garment with sleeves during the full-fashioned weaving process of the present invention. Only one thread or set of threads is interlaced helically and continuously on the front and back for making the tubular section of the fabric and any garment fashioned therefrom.

Figure 2:
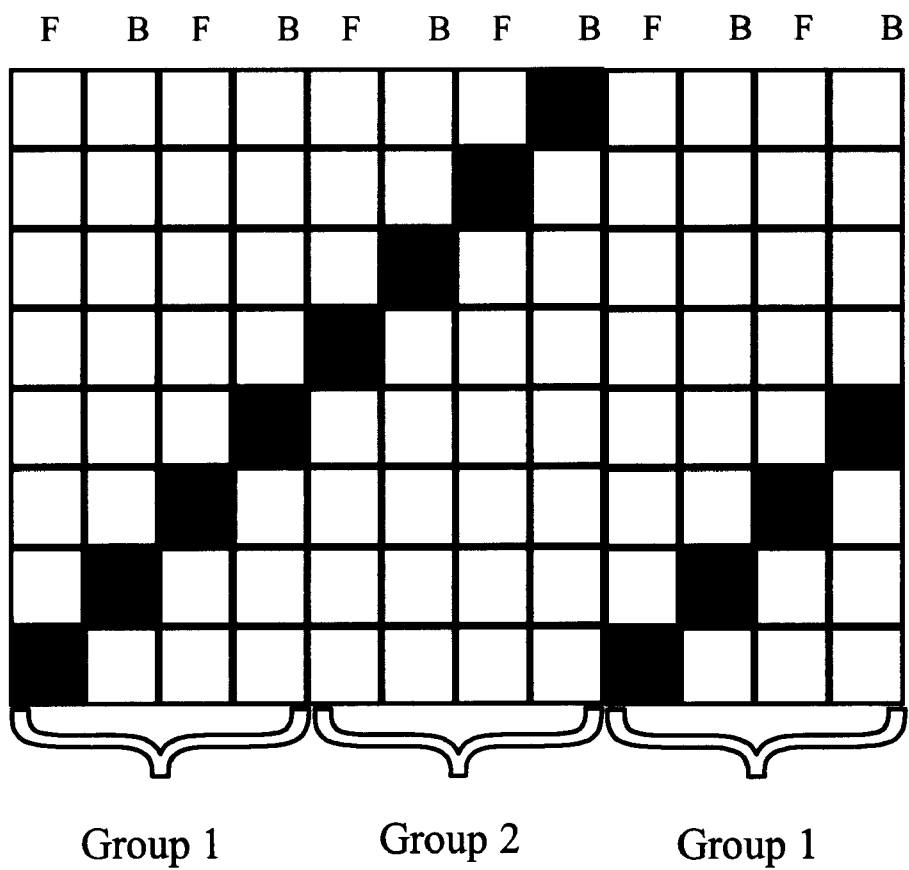
FIG. 2 illustrates the drawing-in-draft for the garment of FIG. 1.

FIG. 2 shows the drawing-in draft for the garment. The drawing-in draft indicates the pattern in which the warp ends are arranged in their distribution over the harness frames. In the drawing-in draft, two different sets of threads are used alternately one is for the front F and the other is for the back B of the garment. The lifting plan in FIG. 3 defines the selection of harnesses to be raised or lowered on each successive insertion of the pick or filling. The harnesses of the loom are lifted by the lifting plan representing the front and back of the garment alternately. Since this is a double cloth structure, both the front and back warp threads are placed in the same dent of the reed of the loom.

Figure 3:
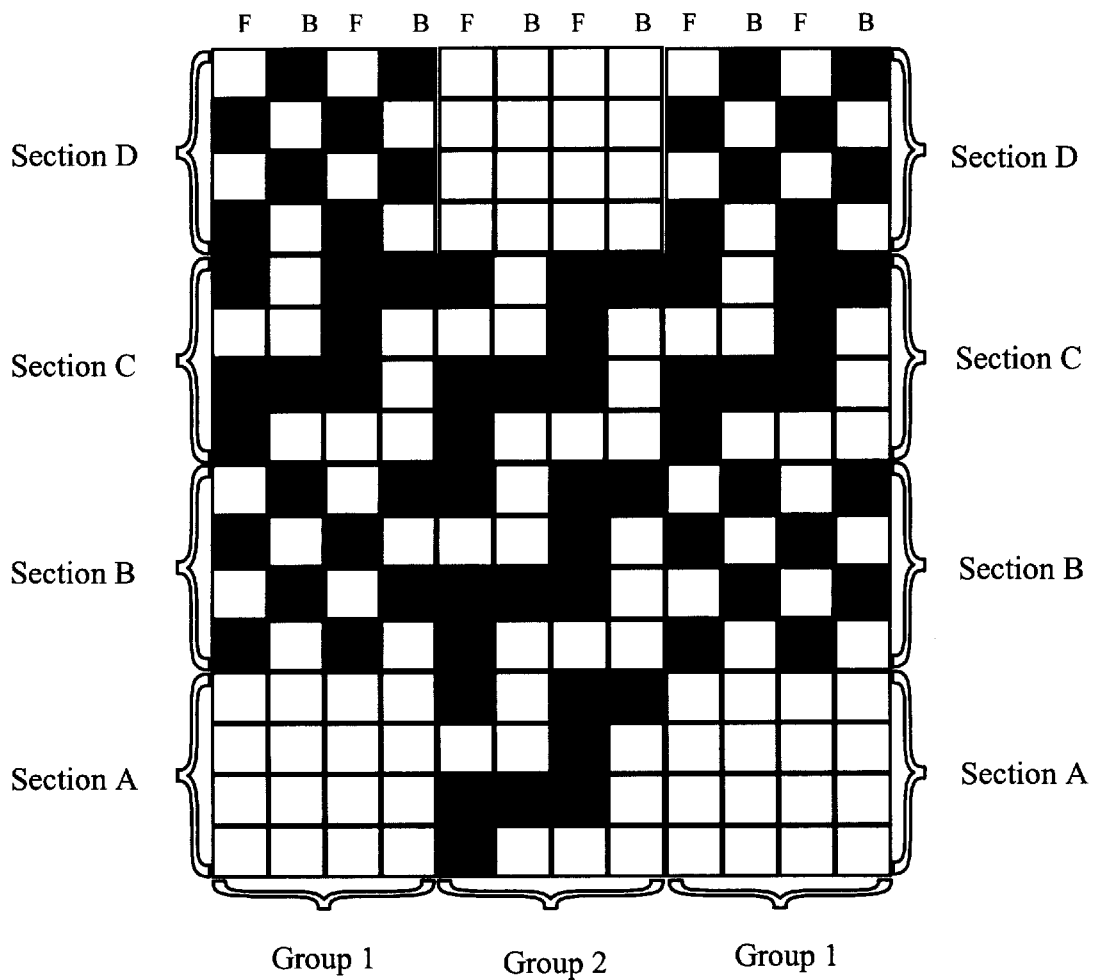
FIG. 3 illustrates the lifting plan for the garment of FIG. 1.

Section A of the garment in FIG. 1 is created by the lifting sequence of the warp threads (also denoted as Section A) in FIG. 3. The warp threads in Group 1 (shown on either side of Group 2 in FIG. 3) are involved in the creation of the sleeves at either end of the body of the garment formed by the warp threads in Group 2.

Although the filling for a tubular fabric needs only one set of continuous threads, in one embodiment the full-fashioned woven garment of the present invention makes use of two sets of threads. This is due to the innovative nature of integrated sleeves.

2. Description of Sleeves of the Garment

One innovative facet of our full-fashioned woven garment lies in the creation of a sleeve by way of the self-stitched layer structure section of the garment in combination with the double layer structure section. Unlike the tubular structure section, in the double layer structure section of the garment, there are two sets of threads, and a double-layer structure is used separately for the front and back of the garment. Since two sets of threads are used from the tubular structure section, the fabric of the self-stitched layer section in combination with the double layer structure section can be woven continuously from the tubular structure section. Then a stand-alone double layer structure section can be woven from this combination self-stitched—double layer structure section. The stand-alone double layer structure section can then be followed continuously by another combination self-stitched—double layer structure section Section B of the garment in FIG. 1 is created by the lifting sequence of the warp threads (also denoted as Section B) in FIG. 3 and this results in the combination self-stitched—double layer structure section creating the closure of the sleeves to be formed by the lifting sequence marked Section C in FIG. 3. The sleeves and body of the garment are also denoted in FIG. 1 as Section C, which is a stand-alone double layer structure section. Section D of the garment in FIG. 1 is identical to Section B and is formed by the lifting sequence marked Section D in FIG. 3 and results in the closure of the sleeves of the garment.

Tubular weaving is a special variation of traditional weaving in which a fabric tube is produced on the loom. This technology has been chosen over traditional weaving for producing our full-fashioned woven garment because cutting and sewing of the fabric will be obviated (with the exception, for example, of rounding or finishing the neck required for fashioning a shirt at the present time), and the resulting structure will be similar to a regular sleeved undershirt, i.e., without any seams at the sides. ft should be understood by those skilled in the art that the garment may be further fashioned by attaching a collar.

The base structure of the fabric is preferably a plain weave (other weaves, however, can be used depending on the application). The warping sequence on the weaving machine (loom) is set for a "block weave" so that the desired groups of yarns can be dropped when necessary. The combination self-stitched—double layer structure is used to form the sleeves without any seams in the garment.

A loom that permits the production of such a woven garment is the AVL Compu-Dobby, a shuttle loom that can be operated both in manual and automatic modes. It can also be interfaced with computers so that designs created using design software can be downloaded directly into the shed control mechanism. Alternatively, ajacquard loom may also be used. Since a dobby loom has been used, the production of the woven fabric on such a loom will be described. One loom configuration for producing the woven garment is:

| Parameter | Details |
| --- | --- |
| Loom Model | AVL Industrial Dobby Loom |
| Loom Description | Computer Controlled Dobby |
| Width | 60 Inches |
| Number of Harnesses | 24 |
| Dents/Inch | 10 |
| Take-Up Mechanism | Automatic Cloth Storage System |

The following steps can be followed for producing a woven garment with sleeves in accordance with our present invention.

1. Enter the weave pattern in the design software and download it into the AVL Compu-Dobby.
2. Prepare 160 Pirns for 2-inch spacing sectional warp beam.
3. Warp yarns onto sectional warp beam 22-inches wide.
4. Install the required number of drop wires.
5. Draw-in 1600 ends through the drop wires.
6. Draw-in 1600 ends through the heddles of 24 harnesses with specific sequences based on the defined weave pattern.
7. Draw 1600 ends through the reed.
8. Tie ends onto weaver's beam on each end.
9. Prepare 8 bobbins for filling with 2 shuttles.

The 24 harnesses of the loom are divided into two sets. Each set contains 12 harnesses. Among the 12 harnesses in each set, six harnesses are used for the front layer and the other six are used for the back layer of the garment. Since the sequence of drawing-in for both sides of the garment is the same, sleeves will be created simultaneously on both sides of the garment.

It will be apparent to one skilled in the art that production of the woven garment in accordance with our present invention is not limited to using a weaving loom having 24 harnesses. For example, a 48 harness loom or a 400 hook jacquard loom machine can also be used.

The woven garment may be made of any yarn applicable to conventional woven fabrics. The choice of material for the yarn will ordinarily be determined by the end use of the fabric and will be based on a review of the comfort, fit, fabric hand, air permeability, moisture absorption and structural characteristics of the yarn. Suitable yarns include, but are not limited to, cotton, polyester/cotton blends, microdenier polyester/cotton blends and polypropylene fibers such as Meraklon (made by Dawtex Industries).

B. Intelligence Capability in Accordance With the Present Invention

In addition to the advantage of obviating cutting and sewing, the woven garment and process of the present invention may provide the basis for a sleeved garment with intelligence capability. As such, the garment can be provided with means for monitoring body physical signs, such as blood pressure, heart rate, pulse and temperature, as well as for monitoring garment penetration. A garment with such intelligence capability consists of the following components: the base of the fabric or "comfort component," and an information infrastructure component. Additionally, a form-fitting component and a static dissipating component may be included, if desired.

The information infrastructure component can include any or all of the following, individually or in any combination: penetration detection components, electrically conductive components, sensors, processors, or wireless transmission devices. The information infrastructure component is capable of acquiring, processing and transmitting information from the subject to a local or remote monitoring unit.

Figure 4:
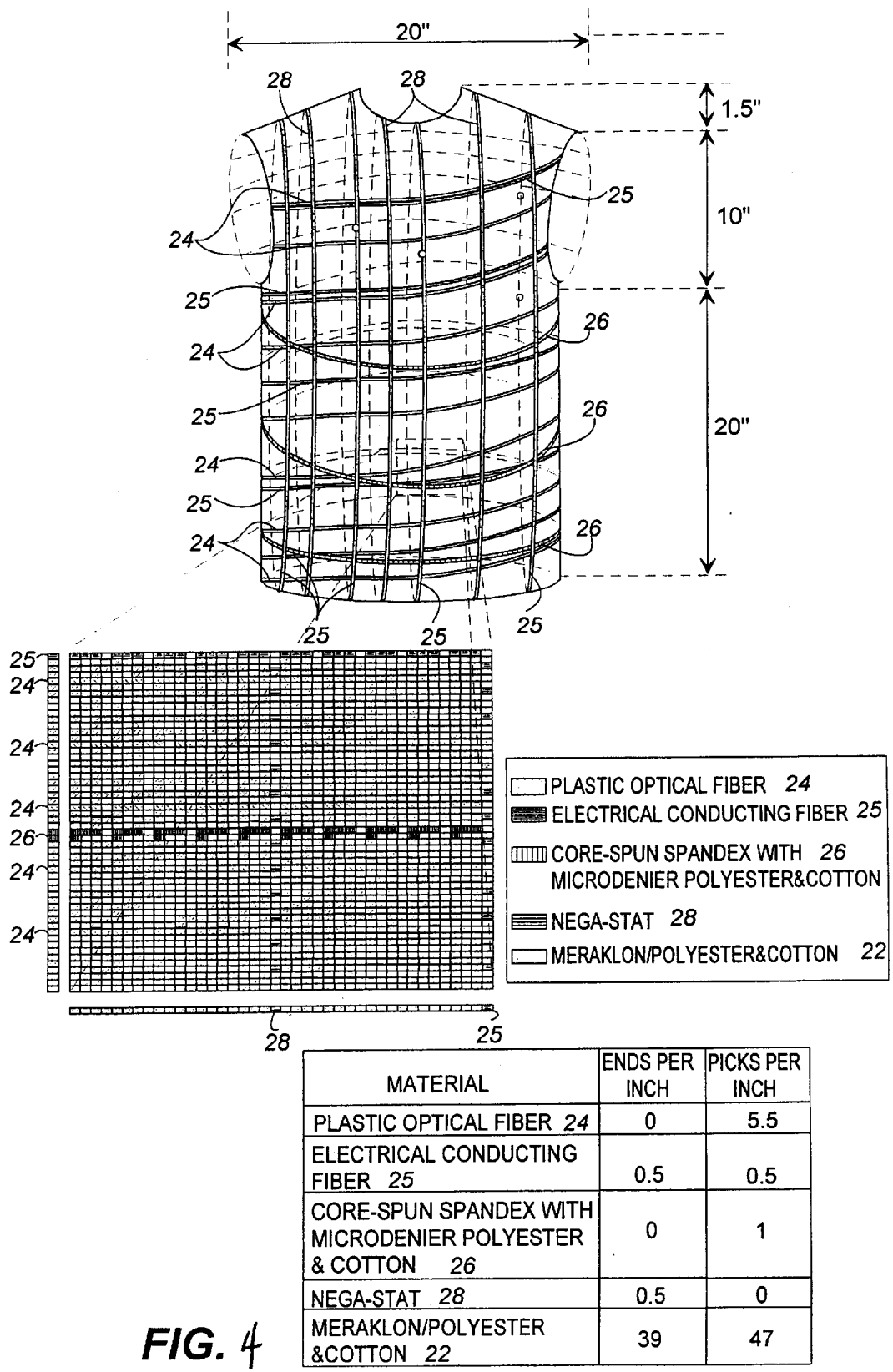
FIG. 4 illustrates a further embodiment of the present invention in the form of a garment having intelligence capability.

FIG. 4 shows one representative design of the garment 20 of the present invention. It consists of a single-piece garment woven and fashioned as described above and is similar to a regular T-shirt. The legend in the figure denotes the relative distribution of yarns for the various structural components of the garment in a 2" segment.

The comfort component 22 is the base of the fabric. The comfort component will ordinarily be in immediate contact with the wearer's skin and will provide the necessary comfort properties for the garment. Therefore, the chosen material should provide at least the same level of comfort and fit as compared to a typical undershirt, e.g., good fabric hand, air permeability, moisture absorption and stretchability.

The comfort component can consist of any yarn applicable to conventional woven fabrics. The choice of material for the yarn will ordinarily be determined by the end use of the fabric and will be based on a review of the comfort, fit, fabric hand, air penneability, moisture absorption and structural characteristics of the yarn. Suitable yarns include, but are not limited to, cotton, polyester/cotton blends, microdenier polyester/cotton blends and polypropylene fibers such as MERAKLON (made by Dawtex Industries).

The major fibers particularly suitable for use in the comfort component are MERAKLON, and polyester/cotton blend including microdenier polyester/cotton. MERAKLON is a polypropylene fiber modified to overcome some of the drawbacks associated with pure polypropylene fibers. Its key characteristics in light of the performance requirements are: (a) good wickability and comfort; (b) bulk without weight; (c) quick drying; (d) good mechanical and color fastness properties; (e) non-allergenic and antibacterial characteristics; and (f) odor-free with protection against bacterial growth. Microdenier polyester/cotton blends are extremely versatile fibers and are characterized by: (a) good feel, i.e., handle; (b) good moisture absorption; (c) good mechanical properties and abrasion resistance; and (d) ease of processing. It should be recognized that other fibers meeting such performance requirements arc also suitable. Microdenier polyester/cotton blended fibers are available from Hamby Textile Research of North Carolina. Microdenier fibers for use in the blend are available from DuPont. MERAKLON yarn is available from Dawtex, Inc., Toronto, Canada. In FIG. 2, MERAKLON is shown in both the warp and fill directions of the fabric.

The sensing component of the garment can include materials for sensing penetration of the garment 24, or one or more body physical signs 25, or both. These materials are woven during the weaving of the comfort component of the fabric. After fashioning of the garment is completed, these materials can be connected to a monitor (referred to as a "personal status monitor" or "PSM") which will take readings from the sensing materials, monitor the readings and issue an alert depending upon the readings and desired settings for the monitor, as described in more detail below.

Materials suitable for providing penetration sensing and alert include: silica-based optical fibers, plastic optical fibers, and silicone rubber optical fibers. Suitable optical fibers include those having a filler medium which have a bandwidth which can support the desired signal to be transmitted and required data streams. Silica-based optical fibers have been designed for use in high bandwidth, long-distance applications. Their extremely small silica core and low numerical aperture (NA) provide a large bandwidth (up to 500 mhz*km) and low attenuation (as low as 0.5 dB/km). However, such fibers are not preferred because of high labor costs of installation and the danger of splintering of the fibers.

Plastic optical fibers (POF) provide many of the same advantages that glass (silica-based) fibers do, but at a lower weight and cost. In certain fiber applications, as in some sensors and medical applications, the fiber length used is so short (less than a few meters) that the fiber loss and fiber dispersion are of no concern. Instead, good optical transparency, adequate mechanical strength, and flexibility are the required properties and plastic or polymer fibers are preferred. Moreover, plastic optical fibers do not splinter like glass fibers and, thus, can be more safely used in the liner than glass fibers.

For relatively short lengths, POFs have several inherent advantages over glass fibers. POFs exhibit relatively higher numerical aperture (NA), which contributes to their capability to deliver more power. In addition, the higher NA lowers the POF's susceptibility to light loss caused by bending and flexing of the fiber. Transmission in the visible wavelengths range is relatively higher than anywhere else in the spectra. This is an advantage since in most medical sensors the transducers are actuated by wavelengths in the visible range of the optical spectra. Because of the nature of its optical transmission, POF offers similar high bandwidth capability and the same electromagnetic immunity as glass fiber. In addition to being relatively inexpensive, POF can be terminated using a hot plate procedure which melts back the excess fiber to an optical quality end finish. This simple termination combined with the snap-lock design of the POF connection system, which connection system can be a conventional connection system, allows for the termination of a node in under a minute. This translates into extremely low installation costs. Further, POFs can withstand a rougher mechanical treatment displayed in relatively unfriendly environments. Applications demanding inexpensive and durable optical fibers for conducting visible wavelengths over short distances are currently dominated by POFs made of either poly-methyl-methacrylate (PMMA) or styrene-based polymers.

Silicone rubber optical fibers (SROF), a third class of optical fibers, provide excellent bending properties and elastic recovery. However, they are relatively thick (of the order of Smm) and suffer from a high degree of signal attenuation. Also, they are affected by high Ihumidity and are not yet commercially available. Hence, although these fibers are not preferred for use in the garment of the present invention, they can be used. Those fibers can be obtained from Oak Ridge National Lab, Oak Ridge, Tenn.

In FIG. 4, the sensing component, here POF, 24 is shown in the filling direction of the fabric, though it need not be limited to only the filling direction. To incorporate a penetration sensing component material into the woven fabric, the material, preferably plastic optical fiber (POF), is spirally integrated into the structure during the full-fashioned weaving fabric production process. The POF does not terminate under the armhole. Due to the above-described modification in the weaving process, the POF continues throughout the fabric without any discontinuities. This results in only one single integrated fabric and no seams insofar as the POF is concerned. The preferred plastic optical fiber is from Toray Industries, New York, in particular product code PGU-CD-501-10-E optical fiber cord. Another POF that can be used is product code PGS-GB 250 optical fiber cord from Toray Industries.

Alternatively, or additionally, the sensing component may consist of an electrical conducting material component (ECC) 25. The electrical conductive fiber preferably has a resistively of from about $0.07 \times 10^{-3}$ to 10 Kohms/cm. The ECC 25 can be used to monitor one or more body vital signs including heart rate, pulse rate, temperature and blood pressure through sensors on the body and for linking to a personal status monitor (PSM). Suitable materials include, but are not limited to, the three classes of intrinsically conducting polymers described below, doped inorganic fibers and metallic fibers.

Polymers that conduct electric currents without the addition of conductive (inorganic) substances are known as "intrinsically conductive polymers" (ICP). Electrically conducting polymers have a conjugated structure, i.e., alternating single and double bonds between the carbon atoms of the main chain. In the late 1970s, it was discovered that polyacetylene could be prepared in a form with a high electrical conductivity, and that the conductivity could be further increased by chemical oxidation. Thereafter, many other polymers with a conjugated (alternating single and double bonds) carbon main chain have shown the same behavior., e.g., polythiophene and polypyrrole. In the beginning, it was believed that the processability of traditional polymers and the discovered electrical conductivity could be combined. However, it has been found that the conductive polymers are rather unstable in air, have poor mechanical properties and cannot be easily processed. Also, all intrinsically conductive polymers are insoluble in any solvent, and they possess no melting point or other softening behavior. Consequently, they cannot be processed in the same way as normal thermoplastic polymers and are usually processed using a variety of dispersion methods. Because of these shortcomings, fibers made up of fully conducting polymers with good mechanical properties are not yet commercially available and hence are not presently preferred for use in the present invention, although they can be used.

Yet another class of conducting fibers consists of those that are doped with inorganic or metallic particles. The conductivity of these fibers is quite high if they are sufficiently doped with metal particles, but this would make the fibers less flexible. Such fibers can be fused to carry information from the sensors to the monitoring unit if they are properly insulated.

Metallic fibers, such as copper and stainless steel insulated with polyethylene or polyvinyl chloride, can also be used as the conducting fibers in the fabric. With their exceptional current carrying capacity, copper and stainless steel are more efficient than any doped polymeric fibers. Also, metallic fibers are strong, and they resist stretching, neck-down, creep, nicks and breakage very well. Therefore, metallic fibers of very small diameter (of the order of 0.1 mm) will be sufficient to carry information from the sensors to the monitoring unit. Even with insulation, the fiber diameter will be less that 0.3 mm and hence these fibers will be very flexible and can be easily incorporated into the fabric. Also, the installation and connection of metallic fibers to the PSM unit will be simple and there will be no need for special connectors, tools, compounds and procedures.

One example of a high conductive yarn suitable for this purpose is Begin available from Bekaert Corporation, Marietta, Ga., a subsidiary of Bekintex Nev., Wetteren, Belgium, which is made up of stainless steel fibers and has a resistively of 60 ohm-meter. The bending rigidity of this yarn is comparable to that of the polyamide high-resistance yarns and can be easily incorporated into the data bus in our present invention.

Thus, the preferred electrical conducting materials for the sensing component for the garment of the present invention are: (i) doped inorganic fibers with polyethylene, nylon or other insulating sheath; (ii) insulated stainless steel fibers; and (iii) thin copper wires with polyethylene sheath. All of these fibers can readily be incorporated into the garment and can serve as elements of an elastic printed circuit board, described below. An example of an available doped inorganic fiber is X-Static coated nylon (T66) from Sauquoit Industries, South Carolina. An example of an available thin copper wire is 24 gauge insulated copper wire from Ack Electronics, Atlanta, Ga.

The electrical conducting component fibers 25 can be incorporated into the woven fabric in two ways: (a) regularly spaced yarns acting as sensing elements; and (b) precisely positioned yarns for carrying signals from the sensors to the PSM. They can be distributed both in the warp and filling directions in the woven fabric.

The form-fitting component (FFC) 26 provides form-fit to the wearer, if desired. More importantly, it keeps the sensors in place on the wearer's body during movement. Therefore, the material chosen should have a high degree of stretch to provide the required form-fit and at the same time, be compatible with the material chosen for the other components of the garment. Any fiber meeting these requirements is suitable. The preferred form-fitting component is SPANDEX fiber, a block polymer with urethane groups. Its elongation at break ranges from 500 to 600% and, thus, can provide the necessary form-fit to the garment. Its elastic recovery is also extremely high (99% recovery from 2–5% stretch) and its strength is in the 0.6–0.9 grains/denier range. It is resistant to chemicals and withstands repeated machine washings and the action of perspiration. It is available in a range of linear densities.

The SPANDEX band 26 shown in the filling direction in FIG. 4 is the FFC for the tubular woven fabric providing the desired form-fit. These bands behave like "straps", but are unobtrusive and are well integrated into the fabric. There is no need for the wearer to tie something to ensure a good fit for the garment. Moreover, the SPANDEX band will expand and contract as the wearer's chest expands and contracts during normal breathing. The SPANDEX fibers can be obtained from E.I. du Pont de Nemours, Wilmington, Del.

The purpose of the static dissipating component (SDC) 28 is to quickly dissipate any built-up static charge during the usage of the intelligent garment. Such a component may not always be necessary. However, under certain conditions, several thousand volts may be generated which could damage the sensitive electronic components in the PSM unit. Therefore, the material chosen must provide adequate electrostatic discharge protection (ESD) protection in the fabric.

NEGA-STAT, a bicomponent fiber produced by DuPont is the preferred material for the static dissipating component (SDC). It has a trilobal shaped conductive core that is sheathed by either polyester or nylon. This unique trilobal conductive core neutralizes the surface charge on the base material by induction and dissipates the charge by air ionization and conduction. The nonconductive polyester or nylon surface of NEGA-STAT fiber controls the release of surface charges from the thread to provide effective static control of material in the grounded or ungrounded applications according to specific end-use requirements. The outer shell of polyester or nylon ensures effective wear-life performance with high wash and wear durability and protection against acid and radiation. Other materials which can effectively dissipate static and yet function as a component of a wearable, washable garment may also be used.

Referring again to FIG. 4, the NEGA-STAT fiber 28 running along the height of the shirt, in the warp direction of the fabric, is the static dissipating component (SDC). The proposed spacing is adequate for the desired degree of static discharge. For the woven tubular garment, it will ordinarily, but not necessarily, be introduced in the warp direction of the fabric.

Figure 5:
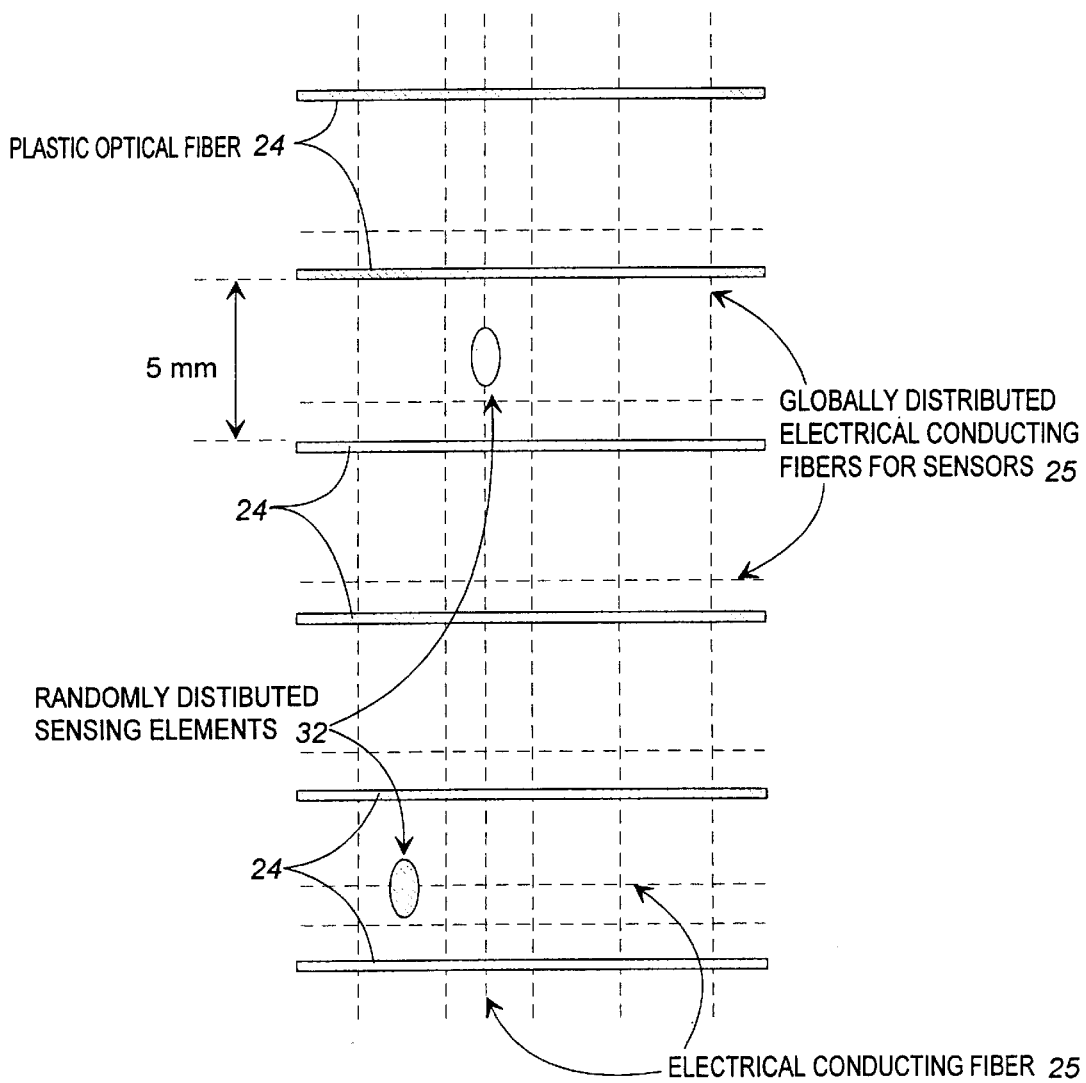
FIG. 5 illustrates the sensor interconnection for the garment of FIG. 4.

With reference to FIG. 5, connectors, such as T-connectors (similar to the "button clips" used in clothing), can be used to connect the body sensors 32 to the conducting fibers that go to the PSM. By modularizing the design of the garment of the present invention (using these connectors), the sensors themselves can be made independent of the garment. This accommodates different body shapes. The connector makes it relatively easy to attach the sensors to the wires. Yet another advantage of separating the sensors themselves from the garment, is that they need not be subjected to laundering when the garment is laundered, thereby minimizing any damage to them. However, it should be recognized that the sensors 32 can also be woven into the structure.

The specification for the preferred materials to be used in the production of the intelligent garment of the present invention are as follows:

| Component | Materials | Count (CC) |
|---|---|---|
| Penetration Sensing (PSC) | Plastic Optical Fibers (POF) | 6s Ne Core-Spun from 12s Ne POF/sheathed from 12s Ne POF |
| Comfort (CC) | Meraklon Microdenier Poly/Cotton Blend | 8s NE |
| Form-fitting (FFC) | Spandex | 8s Ne Core-Spun from 12s Ne Spandex yarn |
| Global and Random Conducting (ECC) | Copper with polyethylene sheath, Doped inorganic fiber with sheath | 6s Ne |
| Static Dissipating (SDC) | Copper with polyethylene sheath, Doped inorganic fiber with sheath | 18s Ne |

The above yarn counts have been chosen based on initial experimentation using yarn sizes that are typically used in undergarments. Other yarn counts can be used. FIG. 4 also shows the specifications for the tubular woven fabric. The weight of the fabric of this embodiment is around 10 oz/yd$^2$ or less. While the above materials are the preferred materials for use in the production of our garment, upon reading this specification it will be readily recognized that other materials may be used in place of these preferred materials and still provide a garment for sensate care in accordance with our present invention.

C. Intelligence Capability of the Garment

The operation of the garment assembly to illustrate its penetration alert and vital signs monitoring capabilities are now discussed.

Penetration Alert:

1. Precisely timed pulses are sent through the POF integrated into the sensing garment.

2. If there is no rupture of the POF, the signal pulses are received by a receiver and an "acknowledgment" is sent to the PSM unit indicating that there is no penetration.

3. If the optical fibers are ruptured at any point due to penetration, the signal pulses bounce back to the first transmitter from the point of impact, i.e., the rupture point. The time elapsed between the transmission and acknowledgment of the signal pulse indicates the length over which the signal has traveled until it reached the rupture point, thus identifying the exact point of penetration.

4. The PSM unit transmits a penetration alert via a transmitter specifying the location of the penetration.

Physical Signs Monitoring:

1. The signals from the sensors are sent to the PSM unit through the electrical conducting component (ECC) of the garment.

2. If the signals from the sensors are within the normal range and if the PSM unit has not received a penetration alert, the physical sign readings are recorded by the PSM unit for later processing.

3. However, if the readings deviate from the normal, or if the PSM unit has received a penetration alert, the physical sign readings are transmitted using the transmitter.

Thus, the proposed intelligent garment is easy to deploy and meets all the functional requirements for monitoring body physical signs and/or penetration. The detection of the location of the actual penetration in the POF can be determined by an Optical Time Domain Reflectometer.

While the invention has been disclosed in its preferred forms, it will be apparent to those skilled in the art that many modifications, additions, and deletions can be made therein without departing from the spirit and scope of the invention and its equivalents as set forth in the following claims.

What is claimed is:

1. A process for continuously weaving a full-fashioned garment with integrated sleeves, comprising the steps of;
   providing at least two sets of warp threads to be used alternately, one set for the front and the other set for the back of the garment;
   providing at least two sets of filling threads;
   weaving a tubular structure section of the garment from the filling and warp threads; a combination self-stitched—double layer structure section continuously from the said tubular structure section; a stand-alone double layer structure section from the said combination self-stitched—double layer structure section; and then a combination self-stitched—double layer structure section from the said stand-alone double layer structure section; and
   the vaxious structure sections being woven continuously one from the other to form the garment.

2. A process as defined in claim 1, wherein the step of weaving the tubular structure section includes interlacing one thread or set of threads helically and continuously on the front and back of the garment.

3. A process as defined in claim 1, further including the step of weaving in a sensing component fiber for providing the capability of monitoring a body vital sign or penetration of the garment.

4. A process as defined in claim 3, wherein the sensing component fiber is selected from the group of either optical fibers and electrical conducting fibers or both.

5. A process as defined in claim 1, further comprising the step of weaving in a form-fitting component fiber.

6. A process as defined in claim 1, further comprising the step of weaving in a static dissipating component fiber.

7. A process as defined in claim 1, wherein the step of weaving the combination self-stitched—double layer sections interspersed with the stand-alone double layer structure section results in sleeves on either side of the garmtmt in said sections.

8. A process as defined in claim 1, wherein the combination self-stitched—double layer structure section is woven continuously from the tubular structures a stand-alone double layer structure section is woven continuously from the combination self-stitched—double layer structure section, and a second combination self-stiched—double layer structure section is woven continuously from the stand-alone double layer structure section.

9. A woven garment with integrated sleeves comprising:
   (a) a tubular structure section;
   (b) a combination self-stitched—double layer structure section woven continuously from the tubular structure;
   (c) a stand-alone double layer structure section woven continuously from the combination self-stitched—double layer structure section; and
   (d) a second combination self-stitched—double layer structure section woven continuously from the stand-alone double layer structure section; and
   (e) the various sections being woven continuously one from the other to form the garment.

10. A woven garment as defined in claim 9, wherein the section formed by the two combination self-stitched—double layer structure sections interspersed with the stand-alone double layer structure section includes sleeves on either side of the garment.

11. Woven garment as defined in claim 9, wherein the tubular structure section includes a thread or set of threads interlaced helically and continuously on the front and back of the garment.

12. A woven garment as defined in claim 9, further comprising a sensing component fiber for providing the capability of monitoring a body vital sign or penetration of the garment.

13. A woven garment as defined in claim 12, wherein the sensing component is selected from the group consisting of either optical fibers and electrical conducting fibers or both.

14. A woven garment as defined in claim 9, further comprising a form-fitting component fiber.

15. A woven garment as defined in claim 9, further comprising a static dissipating component fiber.

16. A woven garment as defined in claim 9, wherein the combination self-stitched—double layer structure section is woven continuously from the tubular structure, a stand-alone double layer structure section is woven continuously from the combination self-stitched—double layer structure section, and a second combination self-stitched—double layer structure section is woven continuously fromt the stand-alone double layer structure section.

17. A woven garment with integrated sleeves comprising:
   (a) a woven structure comprising the following sections: a tubular section; a combination self-stitched—double layer structure section; a stand-alone double layer structure section; and a second combination self-stitched—double layer structure section; and
   (b) a sensing component fiber selected from the group consisting of either optical fibers, electrical conducting fibers, or both.

18. A woven garment with integrated sleeves comprising:
   (a) a woven structure comprising a tubular structure section; a combination self-stitched—double layer structure section woven continuously from the tubular structure; a stand-alone double layer structure section woven continuously from the self-stitched—double layer structure section woven continuously from the stand-alone double layer structure section, the various sections being woven continuously one from the other to form the garment; and
   (b) a sensing component fiber selected from the group consisting of either optical fibers, electrical fibers, or both.

19. A process from continuously weaving a full-fashioned garment with integrated sleeves, comprising the steps of producing each of the following sections: a tubular structure section; a combination self-stitched—double layer structure section; a stand-alone double layer structure section; and a second cobination self-stitched—double layer structure section.

20. A process for continuously weaving a full-fashioned garment with integrated sleeves comprising the steps of:
   weaving a comfort component of the garment comprising the step of weaving a tubular structure section; a combination self-stitched—double layer structure section woven continuously from the tubular structure; a stand-alone double layer structure section woven continuously from the combination self-stitched—double layer structure section; and a second combination self-stitched—double layer structure section woven continuously from the stand-alone double layer structure section, the various sections being woven continuously one from the other to form the garment; and
   weaving a sensing component fiber selected from the group consisting of either optical fibers, electrical fibers, or both into the comfort component of the garment.

* * * * *